United States Patent [19]

Hoelderich et al.

[11] Patent Number: 5,681,973
[45] Date of Patent: Oct. 28, 1997

[54] MICROPOROUS HETEROPOLYOXOMETALLATES AND METHOD OF THEIR PRODUCTION AND USE AS CATALYSTS

[75] Inventors: Wolfgang Hoelderich, Frankenthal; Markus Hoelscher, Aachen; Goetz-Peter Schindler, Mannheim; Ulli Englert, Aachen; Bodo Zibrowius, Wuerselen; Dietrich Arntz, Oberursel, all of Germany

[73] Assignee: Degussa Aktiengesellschaft, Frankfurt am Main, Germany

[21] Appl. No.: 502,261

[22] Filed: Jul. 13, 1995

[30] Foreign Application Priority Data

Jul. 13, 1994 [DE] Germany ............. 44 24 625.0

[51] Int. Cl.$^6$ .............. C07F 19/00; C07F 9/02; C07F 6/00

[52] U.S. Cl. .............. 556/26; 556/28; 556/42; 556/57; 562/512.4; 562/538; 562/590

[58] Field of Search ............. 556/42, 57, 26, 556/28; 562/512.4, 538, 590

[56] References Cited

PUBLICATIONS

Kwon et al., Chemical Abstracts, vol. 111, No. 8, abstract No. 69653t, p. 822 (1989).

*Primary Examiner*—Porfirio Nazario-Gonzalez
*Attorney, Agent, or Firm*—Beveridge, DeGrandi, Weilacher & Young, L.L.P.

[57] ABSTRACT

Heteropolyoxometallates of tungsten, molybdenum and vanadium with a structurally defined micropore volume, a method of production by means of the hydrothermal reaction of the appropriate metal with an associated oxide, a diamine, phosphoric acid and water, and the use of the novel compounds as catalysts.

37 Claims, 1 Drawing Sheet

Structure of $(H_3N(CH_2)_6HN_3)_4(W_{18}P_2O_{62})$

MICROPOROUS HETEROPOLYOXOMETALLATES AND METHOD OF THEIR PRODUCTION AND USE AS CATALYSTS

INTRODUCTION AND BACKGROUND

The present invention relates to heteropolyoxometallates of tungsten, molybdenum and vanadium with a structurally defined micropore volume, a method of their production and their use as catalysts.

As is known, heteropolyoxometallates are polyoxometallate compounds of vanadium, niobium, molybdenum and tungsten, and also, to a lesser extent, of chromium and of tantalum, which can be crystallized by the addition of heteroatoms such as e.g. phosphorus, arsenic, germanium or silicon, either with alkali cations or with organic cations. A survey of the structures of such compounds can be found in M. T. Pope, "Isopoly- and Heteropolyanions", Compr. Coord. Chem., vol. 3 (1987) pp. 1023–1053, editor: Sir G. Wilkinson, or in K. H. Tytko and O. Glemser, Adv. in Inorg. and Radiochem., vol. 19 (1976), pp. 239–315.

Such compounds are customarily obtained by acidifying aqueous solutions of tungstate, molybdenum, vanadate or niobdate. A survey of experimental methods is described in K. H. Tytko and O. Glemser, Adv. in Inorg. and Radiochem., vol. 19 (1976), pp. 239–315. The sodium salts of the corresponding metallates are customarily dissolved in water, in the case of the heteropolyoxometallates the corresponding heteroatom is added in the form of a soluble compound and the solutions obtained in this manner are acidified. After several hours, days or weeks, depending on the degree of acidification and the crystallization temperature, the various compounds are obtained. Typical examples are e.g. the Keggin ions $M_{12}XO_{40}$ or the Dawson ions $M_{18}X_2O_{62}$ (M=Mo, W; X=P, As, Ge, Si). These compounds crystallize with the cited cations as dense phases which exhibit no structurally defined micropore volume.

In the case of molybdenum and vanadium the hydrothermal production of such heteropolyoxometallates and heteropolyoxometallates substituted with organic groups has been previously described; see M. I. Khan, J. Zubieta, J. Am. Chem. Soc., vol. 114 (1992), pp. 10058–10059; M. I. Khan, Q. Chen, H. Hoepke, S. Parkin, C. H. O'Connor, J. Zubieta, Inorg. Chem., vol. 32 (1993), 2929–2937; M. I. Khan, A. Mueller, S. Dillinger, H. Boegge, Q. Chen, J. Zubieta, Angew. Chem., vol. 105 (1993), 1811–1814. However, neither defined micropore volumes nor catalytic applications were found. Moreover, soluble compounds are frequently involved.

SUMMARY OF THE INVENTION

One object of the present invention was to solve the problem of making available heteropolyoxometallates with a defined microporous structure which function in a form-selective manner in catalytic methods.

In achieving the above and other objects, one feature of the present invention resides in heteropolyoxometallates of tungsten, molybdenum and vanadium and heteropolyoxotungstates substituted with vanadium with a structurally defined micropore volume, especially those with a Dawson anion. This includes in particular heteropolyoxometallates of tungsten with the general formula $$(H_3NRNH_3)_{xy/2}(W_{18}P_2O_{62})^x_y \cdot zH_2O \qquad (I)$$

in which x=8 and 12 if y=1,
x=6 and 10 if y=2,
z=1 to 12, especially 1 to 6,
R=—$(CH_2)_n$— and n=1 to 10, preferably 3 to 6, or
R=—$(CH_2—CH_2—NH)_m—CH_2—CH_2$— and m=2 to 6, preferably 2 to 4;

likewise heteropolyoxometallates of molybdenum with the general formula $$(H_3NRNH_3)_{xy/2}(Mo_{18}P_2O_{62})^x_y \cdot zH_2O \qquad (II)$$

in which R, x, y, z have the meanings given above; and the heteropolyoxometallates of vanadium with the general formula $$(H_3NRNH_3)_{xy/2}(W_{18-a}V_aP_2O_{62})^x_y \cdot zH_2O \qquad (III)$$

in which R, x, y, z have the meanings given above and a corresponds to a whole number from 1 to 18, preferably 1 to 10, especially 1 to 6, (V tetravalent), and the empirical formulas naturally always result in an electroneutral compound.

Another feature of the present invention resides in a method of obtaining heteropolyoxometallate compounds with microporous structure by means of hydrothermal crystallization. The compounds of the invention are produced in a synthesis by heating a reaction mixture of metal (powder) and metal oxide or of an oxidic compound of this metal which are present in a ratio of 0.5 to 15 at a pH between 2 and 8 in water. The ratio of the water present in the synthesis mixture to the metal being 3000 to 5000:1. The amines used as spacer either individually or in a mixture with each other have the general formula:

$$H_2N—R—NH_2 \qquad (IV)$$

in which

R=—$(CH_2)_n$— and n=1 to 10, or
R=—$(CH_2—CH_2—NH)_m—CH_2—CH_2$— and m=2 to 6.

The ratio of the above amines to the amount of metal used is between 50 and 25:1 and the ratio of the phosphoric acid to the amount of metal is between 50 and 25:1. The heating is carried out at a temperature of 80° to 250° C. and at a pressure between 3 and 15 bar. The reaction is carried out for a sufficient amount of time until a complete conversion takes place, followed by filtration, washing and drying. The ratio data refers in each instance to molar amounts.

Furthermore, the crystallites produced in accordance with the method of the present invention can be used as catalysts for converting organic molecules and especially as catalysts in oxidation reactions. The method of converting organic compounds involves reacting the organic compounds in the gaseous phase or in the liquid phase with the heteropolyoxometallate as catalyst. For example, the catalytic conversion of organic molecules includes the epoxidation of olefines such as propylene oxide from propylene and $H_2O_2$, the hydroxylation of aromatics such as hydroquinone from phenol and $H_2O_2$, the conversion of alkanes to alcohols, aldehydes and acids, isomerization reactions such as the conversion of epoxides to aldehydes, the splitting of cyclic 1,2 diols to carboxylic acids with $O_2$. In a preferred embodiment, the method of converting organic compounds is a method of oxidizing cyclohexane diol-1,2 to adipic acid which involves reacting cyclohexane diol-1,2 with $H_2O_2$ in the presence of the heteropolyoxometallate as catalyst; for example, the temperature is between 50° and 100° C., the oxygen pressure is 1 bar to 50 bar, the ratio of catalyst to cyclohexane diol-1,2 is between 1:10 and 1:100, and the H₂O₂ solution should be used in a 1.1 to 2.0 -fold excess relative to cyclohexane diol-1,2.

BRIEF DESCRIPTION OF THE DRAWINGS

The present invention will be further understood with reference to the drawing, wherein.

DETAILED DESCRIPTION OF THE INVENTION

Figure 1:
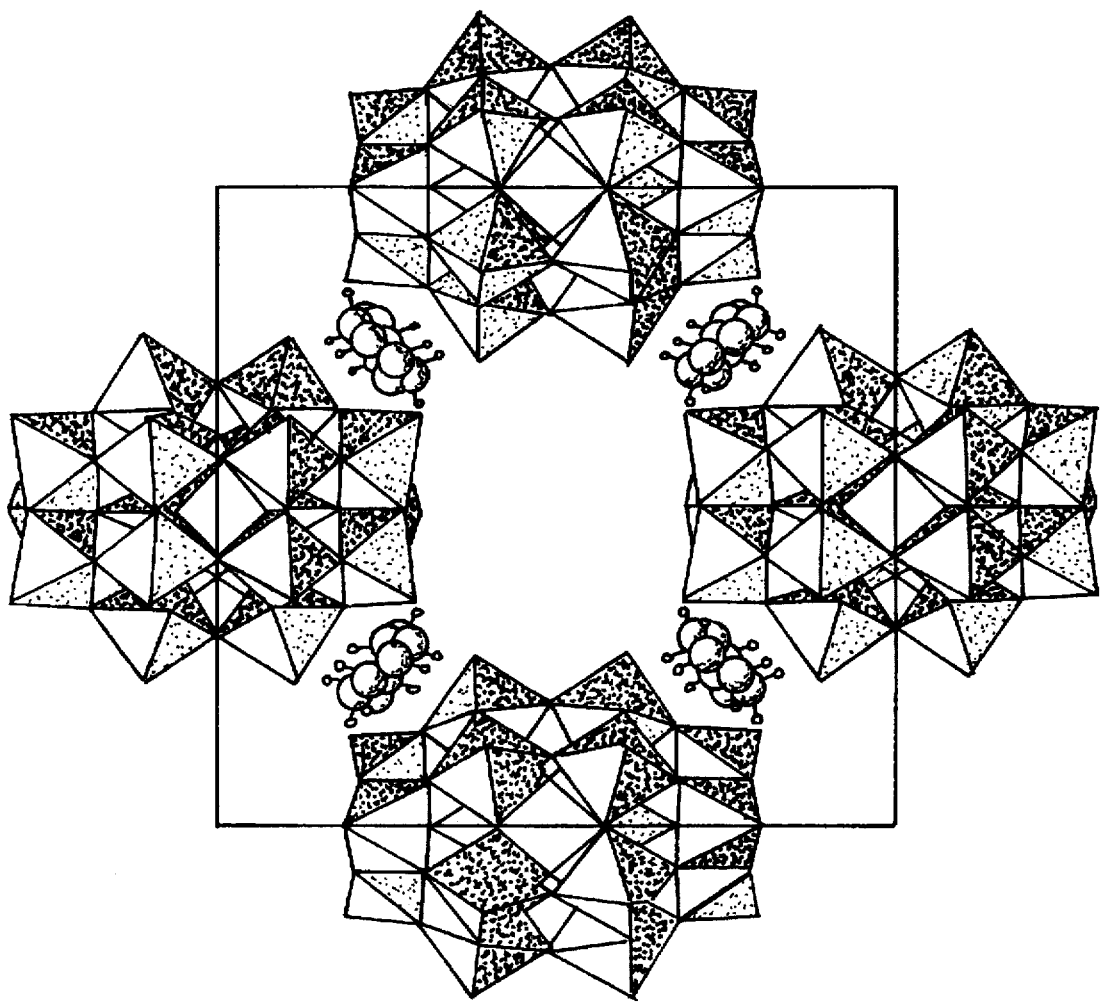
FIG. 1 shows the crystal structure of $(H_3N(CH_2)_6NH_3)_4(W_{18}P_2O_{62})$.

According to a more detailed aspect of the invention, the compounds of the invention are produced in a synthesis by heating a reaction mixture of metal (powder, oxidation state: 0) and metal oxide or of an oxidic compound of this metal (the metal has a positive oxidation state) which are present in a ratio of 0.5 to 15, preferably 1 to 10, especially 3 to 7, at a pH between 2 and 8, preferably 3 and 7, especially 4 and 6, in water. The ratio of the water present in the synthesis mixture to the metal (powder, oxidation state: 0) being 3000 to 5000:1, especially 3200 to 4400:1. The amines used as spacer either individually or in a mixture with each other have the general formula:

$$H_2N{-}R{-}NH_2 \qquad (IV)$$

in which

R=—(CH₂)ₙ— and n=1 to 10, especially 3 to 6, or

R=—(CH₂—CH₂—NH)ₘ—CH₂—CH₂— and m=2 to 6, especially 2 to 4.

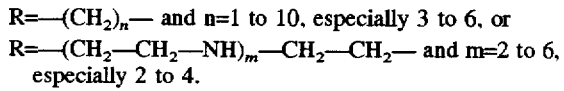

The ratio of the above amines to the amount of metal (powder, oxidation state: 0) used, is between 50 and 25:1, preferably 42 and 35:1.

The ratio of the phosphoric acid to the amount of metal (powder, oxidation state: 0) is between 50 and 25:1, preferably between 40 and 25:1.

The heating is carried out at a temperature of 80° to 250° C., preferably 150° and 230° C., especially 170° and 210° C., and at a pressure between 3 and 15 bar, especially 3 and 7 bar.

The reaction is carried out for a sufficient amount of time until a complete conversion takes place, followed by filtration, washing and drying. The ratio data refers in each instance to molar amounts.

In general, for example, WO₃ and MoO₃ and the corresponding oxide hydrates, but also other oxidic compounds such as e.g. VOSO₄, are used as oxides.

One of the preferred compounds produced in accordance with the invention is tetrakis(1,6-diammonium hexane)-18-tungstenato-diphosphate, $(H_3N(CH_2)_6NH_3)_4(W_{18}P_2O_{62})\cdot 3H_2O$.

The present invention concerns the first production of Dawson anions in a solid with defined micropores. For example, the hydrothermal reaction of tungsten, tungsten oxide (WO₃), hexamethylene diamine, phosphoric acid and water in accordance with the method of the present invention yielded dark blue crystals in 90% yield. Crystal-structure analysis shows the presence of isolated $W_{18}P_2O_{62}$ anions which are surrounded by hexamethylene diamine in such a manner that the protonated amino groups of a molecule combine two Dawson units to each other. There are a total of eight alkyl ammonium groups in the vicinity of an anion; see FIG. 1. In this manner hollow spaces open along the crystallographic c-axis whose shortest O—O intervals are 7.6 and 8.4 Å (diameter from atomic nucleus to atomic nucleus). If one looks along the crystallographic a-axis, the layered construction can be recognized. The polyanions form zig-zag chains parallel to each other and running in the direction of the b-axis in which chains each second or every other anion is at the same height. Between the layers the hexamethylene diamine molecules act as spacers which also leave openings free in the projection with the shortest O—O intervals of 3.6 Å and C—C intervals of 9.1 Å which contain water molecules whose oxygen atoms were able to be localized in the structural analysis. The same applies to the openings in the b-direction, which exhibit dimensions of approximately 3.6×8.7 Å.

In general, the heteropolyoxometallates in accordance with the present invention have micropores with intervals of 3 to 40 Å, especially 4 to 20 Å.

The heteropolyoxotungstates, -molybdates and -vanadates which can be produced in accordance with the present method are used for the catalytic conversion of organic molecules both in the gaseous and in the liquid phase. Conversions of this type are e.g. oxidations. This includes the epoxidation of olefines such as propylene oxide from propylene and H₂O₂, the hydroxylation of aromatics such as hydroquinone from phenol and H₂O₂, the conversion of alkanes to alcohols, aldehydes and acids, isomerization reactions such as the conversion of epoxides to aldehydes, the splitting of cyclic 1,2 diols to carboxylic acids with O₂ as well as further reactions described in the literature with such catalysts such as e.g. in W. F. Hoelderich, "Zeolites: Catalysts for the Synthesis of Organic Compounds", Elsevier, Stud. Surf. Sci. Catal., vol. 49, Amsterdam (1989), pp. 69 to 93, or W. Hoelderich, "New Frontiers in Catalysis", in Proceedings of the 10th International Congress on Catalysis, Budapest (1992), pp. 127 to 163, and especially for possible oxidation reactions such as e.g. in B. Notari in Stud. Surf. Sci. Catal., vol. 37 (1987), pp. 413 to 425, or M. Misono, "New Frontiers in Catalysis", in Proceedings of the 10th International Congress on Catalysis, Budapest (1992), pp. 69 to 101.

Thus, e.g. cyclohexane diol-1,2 can be converted to adipic acid using such catalysts with H₂O₂ as oxidizing agent. The work can be performed e.g. with aqueous H₂O₂ solution at temperatures between 50° and 100° C., especially between 60° and 80° C. and oxygen pressures of 1 bar to 50 bar. The ratio of catalyst to cyclohexane diol-1,2 should be between 1:10 and 1:100, but especially between 1:20 and 1:50. H₂O₂ solution should be used in a 1.1 to 2.0 -fold excess, especially in a 1.3 to 1.6 -fold excess relative to cyclohexane diol-1,2.

The following examples explain the production method of the present invention and the catalytic properties of the heteropolyoxometallates obtained.

EXAMPLE 1

This example describes the production of a crystalline, microporous heteropolyoxotungstate in accordance with the invention using 1,6 diamino hexane:

WO₃, W, hexamethylene diamine (50% in H₂O), H₃PO₄ and H₂O in a molar ratio of 8:1:42:27:4400 were heated for four days at 200° C. in an autoclave provided with a Teflon beaker (250 ml volume) (filling volume of the Teflon beaker about 45%). After filtration, ashlar-shaped, dark blue crystals remained which were washed with H₂O and dried in air. The yield relative to W was between 85 and 95%. Chemical analysis yielded the following values: C=6.97%, N=2.23%, P=1.48% (% by weight).

The compound (tetrakis) 1,6-diammonium hexane)-18-tungstenato-diphosphate, $(H_3N(CH_2)_6NH_3)_4(W_{18}P_2O_{62})$ ·3H$_2$O, produced in accordance with the invention exhibits the following characteristic X-ray diffraction pattern (CuK$_{\alpha 1}$, Siemens D500 powder diffractometer):

| Interplanar interval<br>d (Å) + 0.01 | Relative intensity<br>I/I$_o$ × 100 + 1 |
| --- | --- |
| 13.555 | 100 |
| 12.581 | 65.3 |
| 10.467 | 2.30 |
| 9.284 | 8.86 |
| 7.763 | 6.27 |
| 6.781 | 8.19 |
| 6.193 | 3.45 |
| 5.960 | 15.47 |
| 5.714 | 13.27 |
| 5.376 | 6.32 |
| 5.225 | 7.23 |
| 5.104 | 3.07 |
| 4.861 | 2.11 |

The compound can be labelled orthorhombically with the lattice constants a=19.839, b=18.682, c=12.605 Å. The FTIR spectrum (KBr pellet) of the compound exhibits the following characteristic bands:

| Wave number<br>(cm−1) | Intensity |
| --- | --- |
| 3449 | m* |
| 3130 | m |
| 2930 | m |
| 1860 | m |
| 1080 | m |
| 943 | vs** |
| 912 | vs |
| 819 | vs |

*middle (intermediate)
**very strong

The $^{13}$C- and $^{31}$P-MASNMR measurements (Bruker MSL300 and Bruker MSL500; resonance frequency 75.5 and 202.5 MHz, proton-decoupled) exhibit the following characteristic signals:

| $^{13}$C-MASNMR<br>δ (ppm) | $^{13}$P-MASNMR<br>δ (ppm) |
| --- | --- |
| 27.8 | −1.2 |
| 41.8 | −7.2 |
|  | −13.0 |

The FIR spectrum shows the characteristic oscillation bands of heteropolyoxotungstates, the insertion of the organic spacer and the insertion of phosphorus. The $^{13}$C and $^{31}$P-MASNMR measurements confirm the insertion of phosphorus into the structure of the heteropolyoxometallate anion and the insertion of the amine used as spacer into the structure. The structure of the compound was able to be clarified by X-ray monocrystal structural analysis. It turned out thereby that the compound has defined micropores of different sizes. The largest of these micropores have approximate dimensions of 7.6×8.3 Å (see FIG. 1).

EXAMPLE 2

This example describes the production in accordance with the present invention of a heteropolyoxotungstate using tetraethylene pentamine:

WO$_3$, W, tetraethylene pentamine, H$_3$PO$_4$ and H$_2$O in a molar ratio of 8:1:42:27:4400 were heated four days at 200° C. in an autoclave provided with a Teflon beaker (250 ml volume) (filling volume of the Teflon beaker about 45%). After filtration, needle-like, dark blue crystals remained which were washed with H$_2$O and dried in air. The yield relative to W was between 70 and 80%.

The compound produced in accordance with the invention exhibits the following characteristic X-ray diffraction diagram (CuK$_{\alpha 1 \alpha 2}$, Philips PW 1050/25 powder diffractometer):

| Interplanar interval<br>d (Å) ± 0.1 | Relative intensity<br>I/I$_o$ × 100 + 5 |
| --- | --- |
| 13.01 | 20.7 |
| 11.96 | 65.8 |
| 11.49 | 100.0 |
| 10.17 | 16.4 |
| 6.97 | 5.3 |
| 6.87 | 7.4 |
| 6.42 | 6.8 |
| 6.31 | 7.5 |

The FTIR spectrum (KBr pellet) of the compound exhibits the following characteristic bands:

| Wave number<br>(cm−1) | Intensity |
| --- | --- |
| 3448 | vs |
| 2930 | w* |
| 2860 | w |
| 1077 | m |
| 943 | vs |
| 907 | vs |
| 828 | vs |

*weak

EXAMPLE 3

This example describes the production in accordance with the invention of a heteropolyoxotungstate using triethylene tetramine:

WO$_3$, W, triethylene tetramine, H$_3$PO$_4$ and H$_2$O in a molar ratio of 8:1:42:27:4400 were heated four days at 200° C. in an autoclave provided with a Teflon beaker (250 ml volume) (filling volume of the Teflon beaker about 45%). After filtration, needle-like, dark blue crystals remained which were washed with H$_2$O and dried in air. The yield relative to W was between 70 and 85%.

The compound produced in accordance with the invention exhibits the following characteristic X-ray diffraction diagram (CuK$_{\alpha 1 \alpha 2}$, Philips PW 1050/25 powder diffractometer):

| Interplanar interval<br>d (Å) ± 0.05 | Relative intensity<br>I/I$_o$ × 100 ± 5 |
| --- | --- |
| 13.82 | 22.3 |
| 12.81 | 45.6 |
| 11.94 | 67.4 |
| 11.33 | 100.0 |
| 10.16 | 16.5 |
| 7.76 | 3.4 |
| 6.86 | 7.4 |
| 6.42 | 6.2 |
| 6.19 | 4.8 |
| 5.68 | 3.6 |

The FTIR spectrum (KBr pellet) of the compound exhibits the following characteristic bands:

| Wave number (cm−1) | Intensity |
| --- | --- |
| 3441 | vs |
| 2966 | w |
| 2830 | w |
| 2859 | w |
| 1077 | w |
| 943 | vs |
| 906 | vs |
| 817 | s |

EXAMPLE 4

This example describes the production in accordance with the present invention of a crystalline, microporous heteropolyoxotungstate substituted with vanadium using 1,6-diaminohexane.

$WO_3$, W, hexamethylene diamine (50% in $H_2O$), $H_3PO_4$, $VOSO_4$ and $H_2O$ in a molar ratio of 8:1:42:27:0.8:4400 were heated four days at 200° C. in an autoclave provided with a Teflon beaker (259 ml volume) (filling volume of the Teflon beaker 45%). After filtration, ashlar-shaped, dark blue crystals remained which were washed with $H_2O$ and dried in air. The yield relative to W was between 85 and 95%. Qualitative analysis by means of X-ray fluorescence analysis showed the presence of vanadium.

EXAMPLE 5

This example describes the use of the microporous heteropolyoxotungstate produced in accordance with the invention in the oxidation of cyclohexane diol-1,2 to adipic acid:

0.15 g of the heteropolyoxotungstate produced according to example 1 is added in a round-bottomed flask with reflux condenser to 1.45 g cyclohexane diol-1,2. 5.2 ml of a 30% $H_2O_2$ solution are added thereto. This mixture is heated to 80° C. and agitated 24 hours at this temperature. Hot filtration from the catalyst was carried out. The mother liquor was freeze-dried, the solid produced esterified with diazomethane and the adipic acid methylester produced analyzed with gas chromatography. The yield of adipic acid was 65% at a conversion of 93%.

EXAMPLE 6

This example describes the use of the microporous heteropolyoxotungstate produced in accordance with the present invention in the oxidation of cyclohexane diol-1,2 to adipic acid under slightly elevated oxygen pressure:

0.15 g of the heteropolyoxotungstate of the invention produced according to example 1 are added in a glass autoclave to 1.45 g cyclohexane diol-1,2. 5.2 ml of a 30% $H_2O_2$ solution are added thereto. Then, an $O_2$ pressure of 3 bars is pressed onto the reaction mixture. It was heated to 80° C. and agitated for 24 hours at this temperature. Hot filtration from the catalyst was carried out. The mother liquor was freeze-dried, the solid produced esterified with diazomethane and the adipic acid methylester produced analyzed with gas chromatography. The yield of adipic acid was 78% at a conversion of 93%.

EXAMPLE 7

This example describes the use of the microporous heteropolyoxotungstate produced in accordance with the present invention in the oxidation of cyclohexane diol-1,2 to adipic acid under elevated oxygen pressure:

0.15 g of the heteropolyoxotungstate of the invention produced according to example 1 are added in a steel autoclave to 1.45 g cyclohexane diol-1,2. 5.2 ml of a 30% $H_2O_2$ solution are added thereto. Then, an $O_2$ pressure of 40 bars is pressed onto the reaction mixture. It was heated to 80° C. and agitated for 24 hours at this temperature. Hot filtration from the catalyst was carried out. The mother liquor was freeze-dried, the solid produced esterified with diazomethane and the adipic acid methylester produced analyzed with gas chromatography. The yield of adipic acid was 89% at a conversion of 97%.

While the above examples show W and V, it should be understood that by using the corresponding Mo compounds a heteropolyoxometallate of molybdenum can be produced and utilized.

EXAMPLE 8

This example describes the production in accordance with the present invention of a heteropolyoxomolybdate using hexamethylenediamine: $MoO_3$, Mo, hexamethylenediamine, $H_3PO_4$ and $H_2O$ in a molar ratio of 8:1:42:27:4400 were heated four days at 200° C. in an autoclave provided with a Teflon beaker (250 ml volume). After filtration, inhomogeneous, grey powder reamined.

Further variations and modifications of the foregoing will be apparent to those skilled in the art and such variations and modifications are intended to be encompassed by the claims that are appended hereto.

German Priority Application P 44 24 625.0, filed on 13 Jul. 1994 is relied on and incorporated by reference in their entirety.

We claim:

1. A heteropolyoxometallate of tungsten, molybdenum vanadium having a structurally defined micropore volume with a Dawson anion.

2. A heteropolyoxometallate of tungsten, molybdenum or vanadium having a structurally defined micropore volume and having the formula

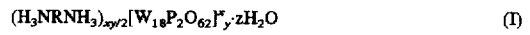  (I)

or having the formula

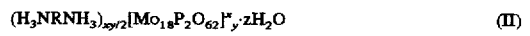  (II)

or having the formula

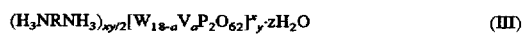  (III)

in which x=8 and 12 if y=1, x=6 and 10 if y=2, z=1 to 12, a=1 to 18,

R=—$(CH_2)_n$—, n=1 to 10,

R=—$CH_2$—$CH_2$—$NH)_m$—$CH_2$—$CH_2$—, m=2 to 6.

3. The heteropolyoxometallate according to claim 2 wherein z=1 to 6.

4. The heteropolyoxometallate according to claim 2 wherein n=3 to 6.

5. The heteropolyoxometallate according to claim 2 wherein m=2 to 4.

6. The heteropolyoxometallate according to claim 2 wherein a=1 to 10.

7. The heteropolyoxometallate according to claim 6 wherein a=1 to 6.

8. The heteropolyoxometallate according to claim 2 having the formula $(H_3N(CH_2)_6NH_3)_4(W_{18}P_2O_{62})\cdot 3H_2O$.

9. The heteropolyoxometallate according to claim 1, wherein said heteropolyoxometallate exhibits micropores with the dimensions 4 to 40 Å along the crystallographic c-axis.

10. The heteropolyoxometallate according to claim 9, wherein said heteropolyoxometallate exhibits micropores with the dimensions 4 to 20 Å along the crystallographic c-axis.

11. A method of producing the heteropolyoxometallate according to claim 1, comprising heating in water a mixture of a metal and of the metal oxide or an oxidic compound of said metal in a ratio of 0.5 to 15, phosphoric acid and at least one amine, wherein said metal is tungsten, molybdenum or vanadium, until a complete conversion occurs, wherein the molar ratio of water to metal is 3000 to 5000:1, said amine being used as spacer individually or in a mixture of amines, said amine having the formula:

$$H_2N\text{—}R\text{—}NH_2 \qquad (IV)$$

in which $R=\text{—}(CH_2)_n\text{—}$ and n=1 to 10, or $R=\text{—}(CH_2\text{—}CH_2\text{—}NH)_m\text{—}CH_2\text{—}CH_2\text{—}$ and m=2 to 6, and the molar ratio of said amine relative to the amount of metal is between 50 and 25:1, and the molar ratio of said phosphoric acid relative to the amount of metal is between 50 and 25:1.

12. The method according to claim 11, wherein said method occurs at a temperature of 80° to 250° C.

13. The method according to claim 12, wherein said heating is at a temperature of 150° to 230° C.

14. The method according to claim 13, wherein said heating is at a temperature of 170° to 210° C.

15. The method according to claim 11, wherein said heating is at a pressure between 3 and 15 bar.

16. The method according to claim 15, wherein said heating is at a pressure between 3 and 7 bar.

17. The method according to claim 11, further comprising filtering off the heteropolyoxometallate.

18. The method according to claim 17, further comprising washing and drying the heteropolyoxometallate.

19. The method according to claim 11, wherein the molar ratio of said metal and of the metal oxide or an oxidic compound of said metal is 1 to 10.

20. The method according to claim 19, wherein the molar ratio of said metal and of the metal oxide or an oxidic compound of said metal is 3 to 7.

21. The method according to claim 11, wherein the pH of said mixture is between 2 and 8.

22. The method according to claim 21, wherein the pH of said mixture is between 3 and 7.

23. The method according to claim 22, wherein the pH of said mixture is between 4 and 6.

24. The method according to claim 11, wherein the molar ratio of water to the metal is 3200 to 4400:1.

25. The method according to claim 11, wherein the molar ratio of the amine to the metal is 42 to 35:1.

26. The method according to claim 11, wherein the molar ratio of the phosphoric acid to the metal is 40 to 25:1.

27. The method according to claim 11, wherein said amine is selected from the group consisting of 1,6 diamino hexane, tetraethylene pentamine, triethylene tetramine, and mixtures thereof.

28. The method according to claim 11, wherein n=3 to 6.

29. The method according to claim 11, wherein m=2 to 4.

30. A method of converting organic compounds, said method comprising reacting cyclohexane diol-1,2 with $H_2O_2$ in the gaseous phase or in the liquid phase with the heteropolyoxometallate according to claim 1 as catalyst.

31. The method according to claim 30, wherein said method involves an oxidation reaction.

32. The method according to claim 30, wherein the temperature is between 50° and 100° C. and the oxygen pressure is 1 bar to 50 bar.

33. The method according to claim 30, wherein the ratio of catalyst to cyclohexane diol-1,2 is between 1:10 and 1:100.

34. The method according to claim 33, wherein the ratio of catalyst to cyclohexane diol-1,2 is between 1:20 and 1:50.

35. The method according to claim 30, wherein between 1:20 and 1:50 $H_2O_2$ solution is used in a 1.1 to 2.0 -fold excess relative to cyclohexane diol-1,2.

36. The method according to claim 30, wherein the temperature is between 60° and 80° C.

37. The method according to claim 30, wherein the oxygen pressure is 1 bar to 50 bar.

* * * * *